United States Patent
Kaneko et al.

(10) Patent No.: US 7,421,108 B2
(45) Date of Patent: Sep. 2, 2008

(54) METHOD AND APPARATUS FOR DETECTING A WORKPIECE, AND METHOD AND APPARATUS FOR INSPECTING A WORKPIECE

(75) Inventors: Tomoyuki Kaneko, Tokyo (JP); Takao Kokubu, Tokyo (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 778 days.

(21) Appl. No.: 10/504,002

(22) PCT Filed: Feb. 21, 2003

(86) PCT No.: PCT/JP03/01915

§ 371 (c)(1),
(2), (4) Date: Aug. 10, 2004

(87) PCT Pub. No.: WO03/071224

PCT Pub. Date: Aug. 28, 2003

(65) Prior Publication Data

US 2005/0058333 A1    Mar. 17, 2005

(30) Foreign Application Priority Data

Feb. 21, 2002    (JP) ............................. 2002-044449

(51) Int. Cl.
*G06K 9/00*    (2006.01)

(52) U.S. Cl. ..................................................... 382/141

(58) Field of Classification Search ......... 382/141–149, 382/274; 348/86, 92
See application file for complete search history.

(56) References Cited

U.S. PATENT DOCUMENTS

| 5,568,564 | A | * | 10/1996 | Ozaki .......................... 382/149 |
| 5,652,432 | A | * | 7/1997 | Yaginuma ............... 250/559.06 |
| 5,703,687 | A | * | 12/1997 | Kumagai et al. ............ 356/426 |
| 7,092,105 | B2 | * | 8/2006 | Lim et al. ................... 356/601 |

FOREIGN PATENT DOCUMENTS

| JP | U 06-84305 | 12/1994 |
| JP | A 11-138654 | 5/1999 |
| JP | A 2001-12920 | 1/2001 |
| JP | A 2001-249012 | 9/2001 |

* cited by examiner

*Primary Examiner*—Daniel G Mariam
(74) *Attorney, Agent, or Firm*—Oliff & Berridge, PLC

(57) ABSTRACT

A tire T as a workpiece mounted on a rotary table 2 is imaged by using floodlight means 10 for applying white slit light and a color CCD camera 20 for imaging a portion illuminated by the slit light while it is turned, the coordinates and brightness of the tire T are detected from the obtained image data by coordinate computing means 31 and brightness computing means 33, and the 3-D coordinate data and color image of the tire T are re-formed from the obtained shape data and brightness data of the tire T by shape image forming means 32 and appearance image forming means 34 and compared with tire appearance and shape data prestored in tire information storage means 35 to judge whether the appearance and shape of the tire T are acceptable or not.

17 Claims, 4 Drawing Sheets

METHOD AND APPARATUS FOR DETECTING A WORKPIECE, AND METHOD AND APPARATUS FOR INSPECTING A WORKPIECE

BACKGROUND OF THE INVENTION

1. Field of the Invention

The present invention relates to a method and apparatus for detecting or inspecting the appearance and shape of a workpiece such as a tire or tire part by imaging it.

2. Description of the Prior Art

In the prior art, as one of product inspection methods, a product is imaged by a line camera to judge whether the surface state such as discoloration or stains of the workpiece is acceptable or not from the obtained appearance data. However, discoloration or stains can be judged accurately from data on the appearance imaged by the line camera but the shape of the workpiece cannot be judged accurately. Therefore, a light-section method in which the surface of the workpiece is imaged by an area camera by applying slit light to detect the shape of the workpiece from the obtained image data is employed.

To inspect the shape of a tire by the above light-section method, as disclosed by JP-A 11-138654 (the term "JP-A" as used herein means an "unexamined published Japanese patent application"), for example, slit light is applied to the surface of the tire by floodlight means such as a semiconductor laser to image a portion illuminated by the above slit light with an area camera, the obtained image data is converted into secondary coordinate values to obtain the outer shape of the tire, and the shape is compared with the pre-stored image of the workpiece to inspect the shape of the tire such as a beat, tread or side wall portion. At this point, the shape and circularity of the tire in a predetermined region can be detected and inspected by turning the floodlight means, the imaging means and the tire relative to one another.

However, in the above light-section method, the circularity, surface unevenness or scratch can be checked but not discoloration and stains. Then, there is proposed an apparatus for imaging the same line portion of a workpiece with a line camera and an area camera at the same time (JP-A 2001-249012). As shown in FIG. 5, this is aimed to inspect the appearance and shape of a tire T mounted on a rotary table 58 turned by a motor 57 at the same time by using imaging means 50 which comprises a floodlight (illuminator) 51 making use of a white LED, line camera 52, line reflection mirror 53, laser floodlight 54 having a wavelength of 680 nm and area camera 55, all built in one holding frame 56, to pick up a slit image of the tire T illuminated by light from the above floodlight 51 with the line camera 52 so as to obtain monochromatic or color appearance data and to input shape data on a ridge line on the surface of the tire T obtained by imaging a portion illuminated by slit light from the laser floodlight 54 with the area camera 55. The above obtained appearance data and shape data are transmitted to the appearance image forming means 61 and shape image forming means 62 of an appearance and shape judging unit 60 to be processed, compared with tire appearance and shape data pre-stored in tire information storage means 65 to judge whether the appearance and shape are acceptable or not, and finally whether the tire is acceptable or not is judged by overall judging means 66.

However, in the above method, the apparatus becomes bulky and it is difficult to optically align a line portion to be imaged by the line camera 52 with a line portion to be imaged by the area camera 55. Although it is possible to align the obtained two images by software, data processing becomes complicated and storage means or computing means for processing data is necessary.

It is an object of the present invention which has been made in view of the above problems of the prior art to provide a method and apparatus for detecting the appearance and shape of a workpiece by imaging the workpiece to detect the coordinates and brightness of the workpiece with a simple structure and a method and apparatus for inspecting the appearance and shape of a workpiece using this detection method.

SUMMARY OF THE INVENTION

In the above light-section method, as shown in FIG. 2($a$), the positions of the gravity centers of a plurality of pixels "s" forming a slit image "S" showing a ridge line on the surface of the tire T which is illuminated and imaged by an area camera are calculated to obtain the 2-D coordinates of each position of the slit image "S".

The inventors of the present invention paid attention to the fact that when a portion having a color different from the color of the base of a tire, such as a stain or discoloration, is included in an illuminated portion, light applied to the tire T has a wide wavelength distribution, the line width of the above slit image "S" becomes nonuniform, and the brightness of each pixel "s" becomes different as shown in FIG. 2($b$) and found that the appearance and shape of the workpiece can be detected from one slit image "S" at the same time by obtaining the density (or color) of the workpiece from data on the brightness of each pixel "s". The present invention has been accomplished based on this finding.

That is, according to a first aspect of the present invention, there is provided a method of detecting the coordinates and brightness of a workpiece, comprising the steps of:

moving a workpiece, floodlight means for applying slit light to the surface to be inspected of the workpiece and imaging means having an area camera for imaging a portion illuminated by the slit light relative to one another to image the workpiece; and detecting the coordinates and brightness of the workpiece from the pixel data of the area camera at the same time.

According to a second aspect of the present invention, there is provided a method of inspecting a workpiece, comprising the steps of:

moving a workpiece, floodlight means for applying slit light to the surface to be inspected of the workpiece and imaging means having an area camera for imaging a portion illuminated by the slit light relative to one another to image the workpiece; and inspecting the workpiece based on the coordinates and brightness of the workpiece calculated from the pixel data of the area camera.

According to a third aspect of the present invention, there is provided a method of inspecting a workpiece, wherein the coordinates and brightness of a specific region of the workpiece are integrated to obtain the shape data and density data of the specific region.

According to a fourth aspect of the present invention, there is provided a method of inspecting a workpiece, wherein the obtained shape data or density data is compared with the reference shape data or reference density data on the specific region of the workpiece to inspect the workpiece.

According to a fifth aspect of the present invention, there is provided a method of inspecting a workpiece, wherein it is judged that the specific region of the workpiece is unacceptable when the size of a region in which the difference between the obtained shape data and reference shape data and/or the difference between the obtained density data and reference density data exceeds a preset threshold value becomes larger than a predetermined value.

According to a sixth aspect of the present invention, there is provided a method of inspecting a workpiece, wherein the workpiece is inspected based on surface unevenness calculated from the obtained shape data or the degree of density calculated from the obtained density data.

According to a seventh aspect of the present invention, there is provided a method of inspecting a workpiece, wherein three white slit beams and a color camera are used to detect the shape and color of the workpiece at the same time.

According to an eighth aspect of the present invention, there is provided an apparatus for detecting the appearance and shape of a workpiece by detecting the coordinates and brightness of the workpiece, comprising:

floodlight means for applying slit light to the surface to be inspected of the workpiece;

an area camera for imaging a portion illuminated by the slit light;

means of moving the floodlight means, the imaging means and the workpiece relative to one another;

means of calculating the coordinates of the workpiece from the pixel data of the area camera;

means of calculating the brightness of the workpiece from the pixel data of the area camera; and means of detecting the appearance of the workpiece based on the calculated brightness.

According to a ninth aspect of the present invention, there is provided an apparatus for detecting a workpiece, wherein white light is used as the slit light and a color camera is used as the imaging means.

According to a tenth aspect of the present invention, there is provided an apparatus for inspecting a workpiece, comprising:

the detection apparatus of the eighth or ninth aspect;

means of storing reference data on the appearance and shape of the workpiece; and means of judging whether the shape and appearance of the workpiece are acceptable or not by comparing data on the appearance and shape of the workpiece obtained by the appearance and shape detection apparatus with the reference data.

DESCRIPTION OF THE PREFERRED EMBODIMENTS

Preferred embodiments of the present invention will be described hereinbelow with reference to the accompanying drawings.

Figure 1:
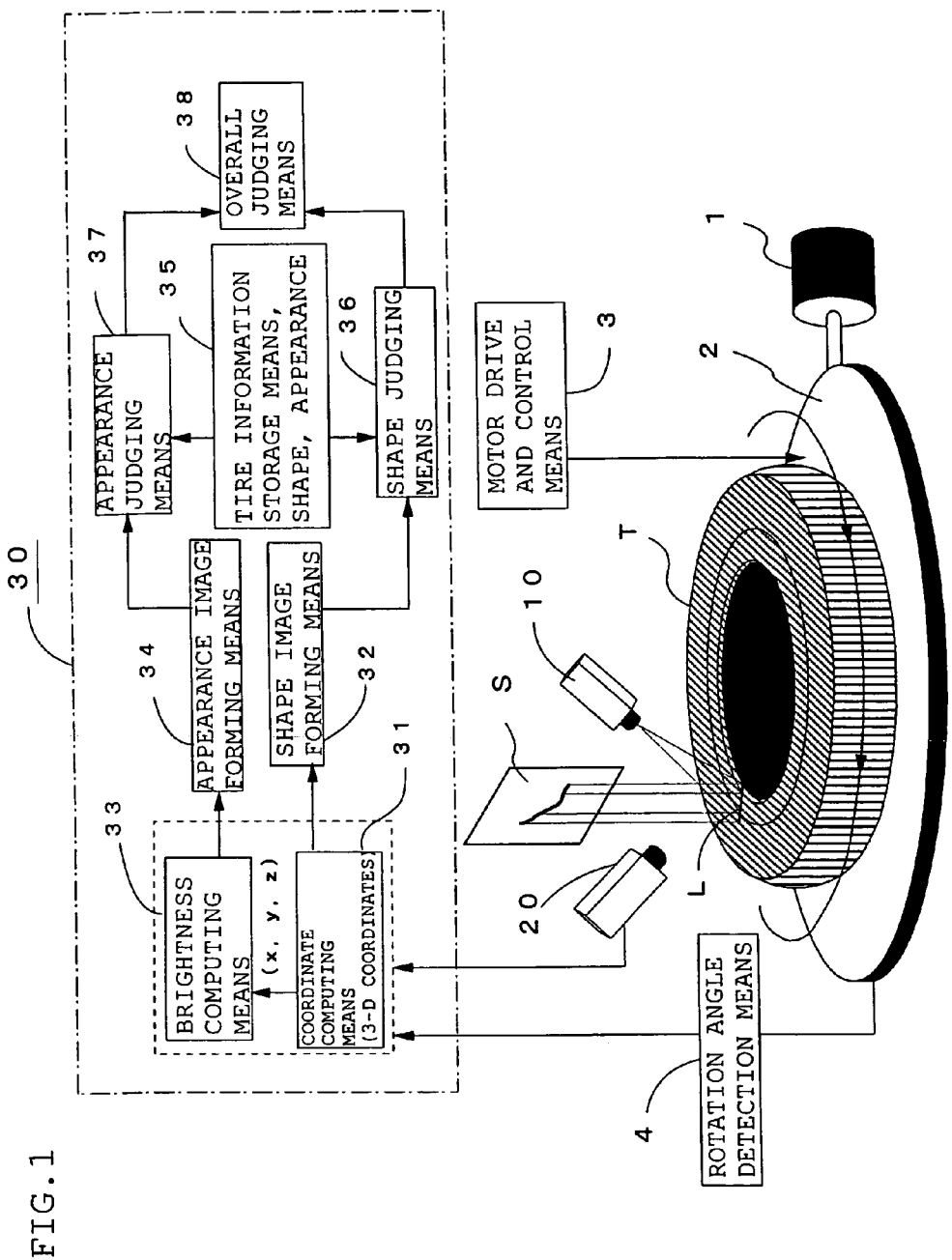
FIG. 1 is a diagram showing the constitution of a tire appearance and shape inspection apparatus according to a preferred embodiment of the present invention.

FIG. 1 is a diagram showing the constitution of a tire appearance and shape inspection apparatus according to a preferred embodiment of the present invention. In FIG. 1, reference numeral 10 denotes floodlight means for applying white slit light to the surface to be inspected of a tire T as a workpiece mounted on a rotary table 2 turned by a motor 1, 20 a color CCD camera, having pixels on a plane, for imaging a portion L illuminated by the above slit light of the turning tire T, 30 a tire judging unit for judging whether the shape and appearance of the above tire are acceptable or not by detecting the shape and appearance of the tire T from an image obtained by the color CCD camera 20, 3 motor drive and control means for driving and controlling the above motor 1, and 4 rotation angle detection means for detecting the rotation angle θ of the tire T by detecting the rotation position of the above rotary table 2.

The tire judging unit 30 comprises coordinate computing means 31 for obtaining data on the 3-D coordinates of the tire T from an image (slit image "S") of a ridge line on the surface of the tire T imaged by the color CCD camera 20 and the rotation angle θ of the tire T detected by the rotation angle detection means 4, shape image forming means 32 for re-forming a 3-D image of the tire T by collecting the above 3-D coordinate data of one round of the tire, brightness computing means 33 for computing brightness data on R, G and B computed from the above slit image "S", appearance image forming means 34 for re-forming a color image of the tire T from the above brightness data and 3-D coordinate data, shape judging means 36 and appearance judging means 37 for comparing the obtained 3-D image and color image of the tire T with the above reference data, and overall judging means 38 for judging whether the tire T is acceptable or not.

A description is subsequently given of the method of inspecting the appearance and shape of the tire with the above apparatus.

The motor 1 is first driven by the motor drive and control means 3 to turn the rotary table 2 mounting the tire T to be inspected, white slit light is applied to the above turning tire T from the floodlight means 10 comprising a white light source such as a white laser or halogen lamp to image the illuminated portion L of the tire T with the color CCD camera 20 so as to obtain image data (slit image "S") on the ridge line on the surface of the tire T, and the image data is sent to the coordinate computing means 31 of the tire judging unit 30.

Figure 2A:
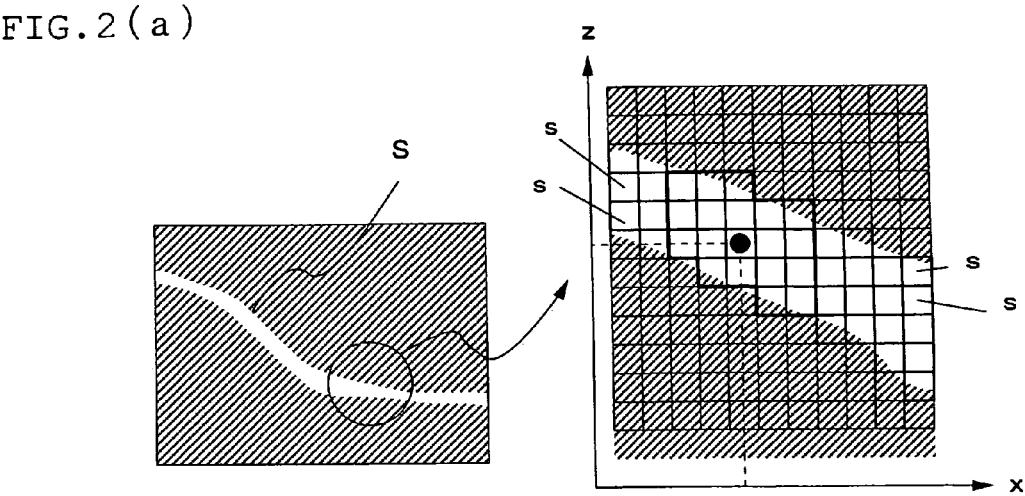
FIGS. 2(a) and 2(b) are diagrams for explaining the measurement principles of the present invention.
Figure 2B:
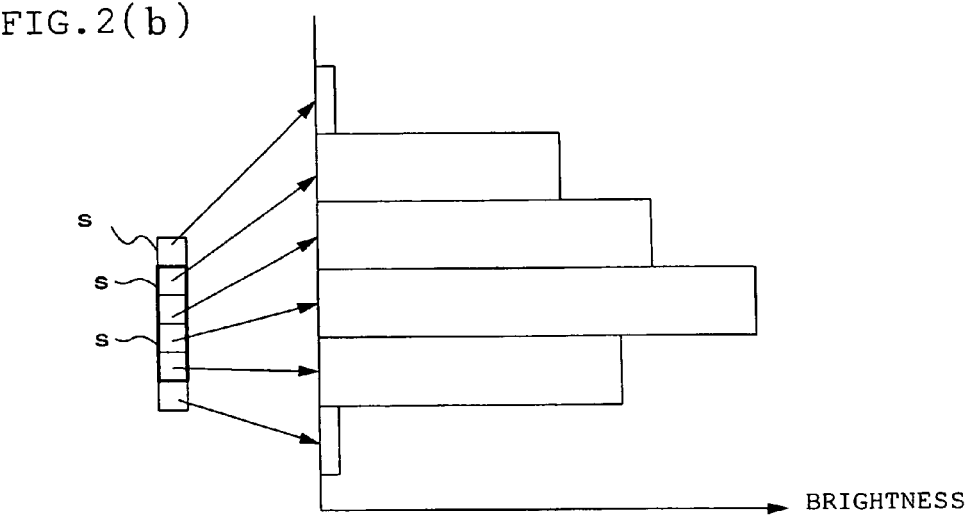

As shown in FIG. 2(a), the coordinate computing means 31 computes the positions of the gravity centers of illuminated pixels "s", out of the plurality of pixels forming the above slit image "S", to obtain the 2-D coordinates (x, z) of each position of the above slit image "S", and the 3-D coordinate data (x, y, z) of the tire T are obtained from the 2-D coordinates (x, z) and the rotation angle θ of the tire T detected by the above rotation angle detection means 4. The shape image forming means 32 computes the above 3-D coordinate data (3-D shape data) of one round of the tire by collecting the slit image "S" for each θ to detect the coordinates of the tire T as the workpiece and process the 3-D data to re-form a 3-D image of the tire T. As shown in FIG. 2(b), the brightness computing means 33 integrates the brightness's of the pixels "s" used for the computation of the above positions of the gravity centers to detect the brightness of the tire T as the workpiece so as to obtain brightness data at the above 3-D coordinate position (x, Y, z).

In the above figures, only one color is shown. In this embodiment, this is made on R, G and B colors to compute brightness data (3-D brightness data) at the 3-D coordinate position (x, y, z). The appearance image forming means 34 processes an image by using the above 3-D coordinate brightness data and the 3-D coordinate data (x, y, z) of the tire T to re-form a color image or shaded image of the tire T.

The 3-D image and color image or shaded image of the tire T which have been processed are compared with tire appearance and shape data pre-stored in the tire information storage means 35 by the shape judging means 36 and the appearance judging means 37 respectively to judge whether the circularity, surface unevenness and scratch, or appearance such as discoloration or stains and shape of the tire are acceptable or not, and the overall judging means 38 finally judges whether the tire is acceptable or not to inspect the tire T as the workpiece.

For the actual inspection of the appearance and shape of the tire, it is not necessary to form the 3-D data or 3-D image of the above tire T and compare all of it with the reference data. For instance, the coordinates and brightness of a specific region such as an inner side portion or inner crown portion are estimated to compute the shape data of the specific region, and the 3-D shape data or 3-D image of the specific region is compared with the tire shape data of the above specific region pre-stored in the tire information storage means 35 to inspect the shape of the above tire T. That is, since shape and size reference values can be set by comparison for each specific region, whether the workpiece is acceptable or not can be judged more easily. The shape of the tire T may be inspected by comparing surface unevenness calculated from the above obtained shape data with the previously set threshold value (reference shape data) instead of comparison with data on the shape of the above tire. Alternatively, whether the shape of the tire is acceptable or not may be judged based on surface unevenness observed from a 3-D image of the tire T.

When the comparison of 3-D density data or color image is made on a wide region to inspect discoloration or stains, or when the above comparison is made on a narrow specific region such as an inner crown portion or shoulder portion to inspect the exposition of a cord, the appearance of the above tire T can be inspected efficiently. Even in this case, the degree of density calculated from density data may be compared with the preset threshold value (reference density data) to inspect the appearance of the above tire T or to judge whether the appearance of the tire is acceptable or not based on the degree of density observed from a color image (or shaded image) of the above tire T in place of comparison with data on the appearance of the above tire.

It may be judged that a specific region is unacceptable when the size of the region in which the difference between the above obtained 3-D shape data and the above tire shape data and/or the difference between the obtained 3-D density data and the above tire appearance data exceed(s) the preset threshold value becomes larger than a predetermined value.

For example, for judgment on the shape of an inner shoulder portion or inner side portion, when a portion having a height larger than a predetermined value exists over a predetermined length or more in a peripheral direction, it is considered that the inner shoulder portion or the inner side portion is unacceptable. For appearance inspection, it is judged that the appearance of the above side portion is unacceptable when a region having a brightness outside a predetermined range considered as a defect has a predetermined area or more in the side portion.

According to this embodiment of the present invention, the tire mounted on the rotary table 2 is imaged by the floodlight means 10 for applying white slit light and the color CCD camera 20 for imaging a portion illuminated by the above slit light while the tire T is turned, and the coordinates and brightness of the above tire T are calculated from the above obtained image data by the coordinate computing means 31 and the brightness computing means 33 to detect the shape and color of the above tire T. Therefore, the shape and appearance of the tire T can be inspected at the same time with a simple structure.

Since the shape and color are detected from a single slit image in the present invention, misregistrations in shape and color caused by the displacement of a line portion which are seen in the prior art do not occur, thereby making it possible to obtain an accurate 3-D image and color image of the tire T.

In the above embodiment, the workpiece is a product tire T. The present invention is not limited to this workpiece and may be a tire or tire constituting member before vulcanization, mechanical part or golf head whose appearance and shape must be inspected.

In the above embodiment, the color CCD camera 20 is used to obtain a color image of the tire T. When an appearance image is a monochromatic image and not satisfactory, one-color slit light and a monochromatic CCD camera may be used to obtain a shaded image of the tire T. To obtain a monochromatic image, a white laser does not need to be used as a light source.

Figure 3:
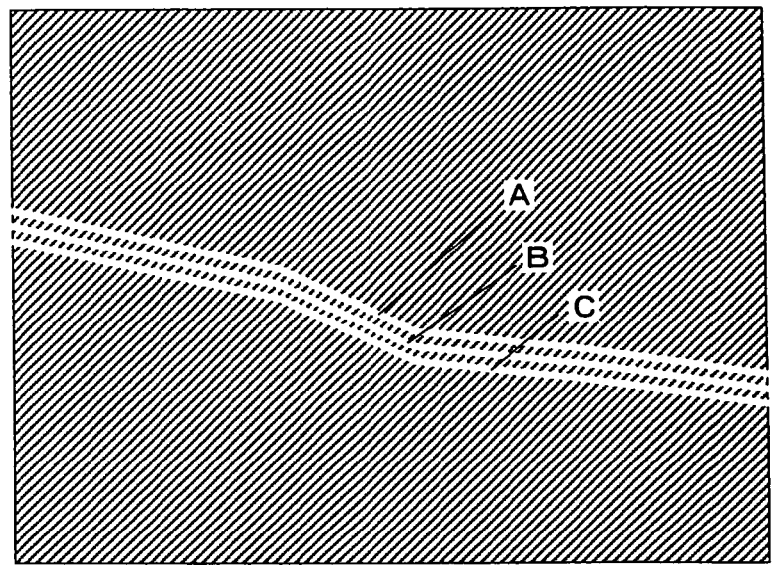
FIG. 3 is a diagram showing another example of the tire appearance and shape inspection method of the present invention.

To obtain a color image, slit beams may be applied to the tire T from R, G and B one-color lasers as light sources at predetermined intervals to take a color image with monochromatic CCD cameras. In this case, three lines (monochromatic images) A, B and C which are shifted from one another by the above time interval are obtained as slit images as shown in FIG. 3. When the brightness's of R, G and B are calculated from these lines, a color image of the tire T can be obtained without using the color CCD camera 20.

Figure 4:
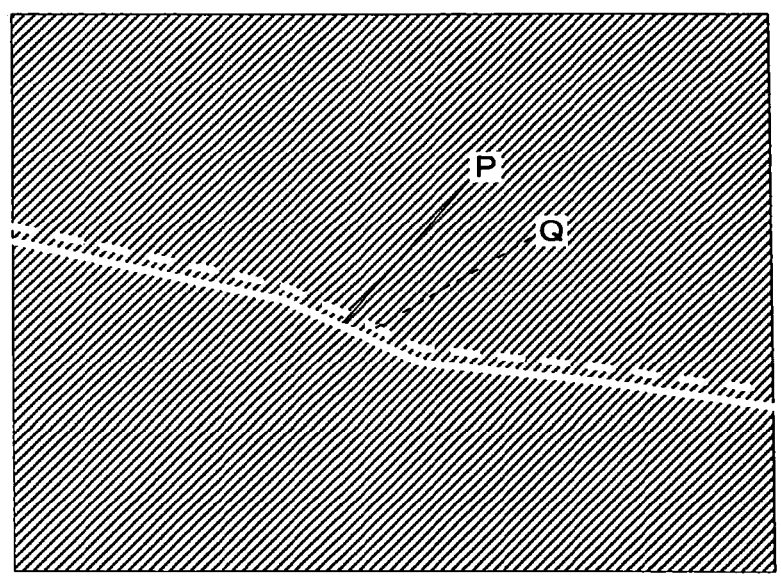
FIG. 4 is a diagram showing still another example of the tire appearance and shape inspection method of the present invention.
Figure 5:
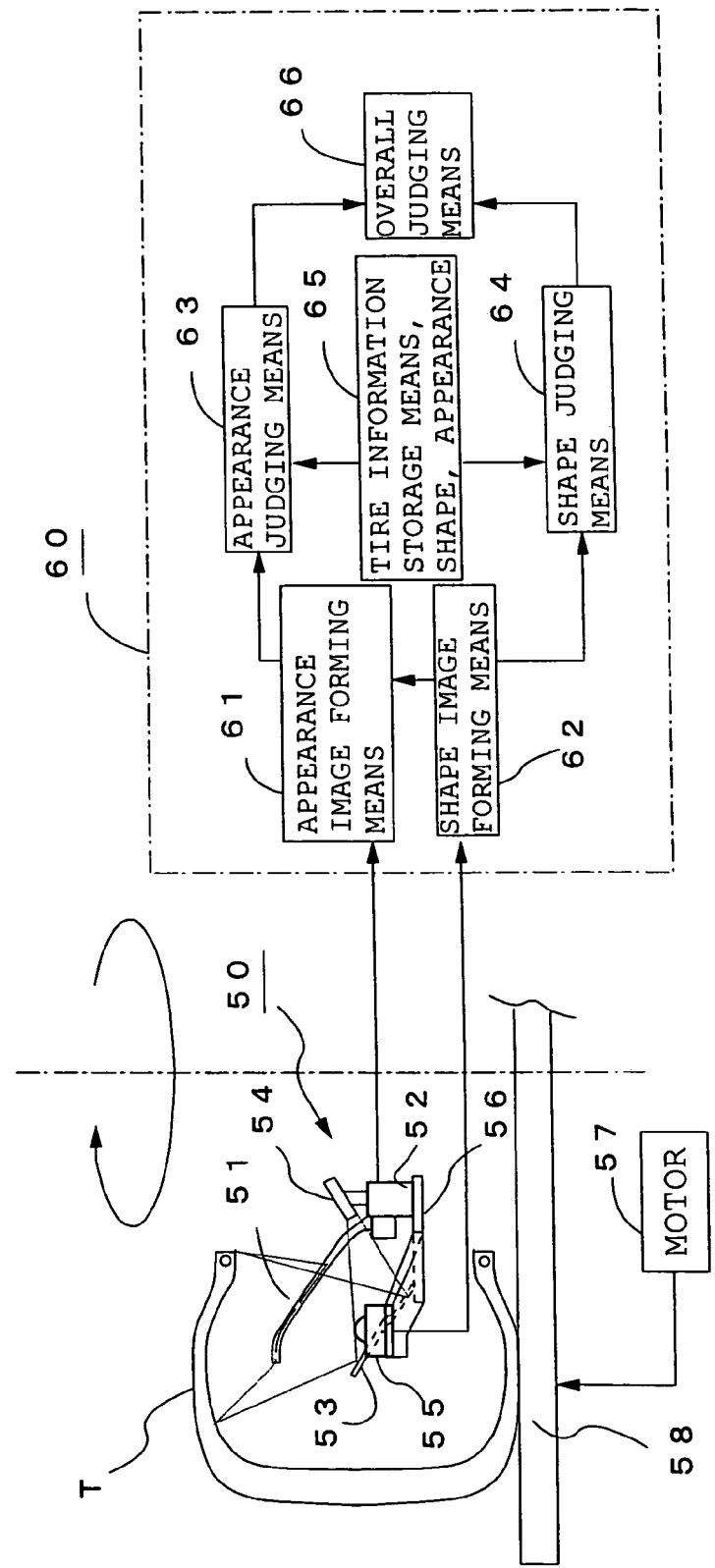
FIG. 5 is a diagram showing the constitution of a tire appearance and shape inspection apparatus of the prior art.

Alternatively, light beams from a one-color laser (R) and G and B one-color LED's as light sources may be used to take a color image with the color CCD camera 20. In this case, a slit image P obtained with the one-color laser and a line Q obtained with the one-color LED's adjacent to the above slit image are obtained as shown in FIG. 4. By computing the coordinates of the tire T from the above slit image P and the brightness's of R, G and B from the above slit image P and the line Q, a color image of the tire T can be obtained.

INDUSTRIAL FEASIBILITY

As described above, according to the present invention, a workpiece, floodlight means for applying slit light to the surface to be inspected of the workpiece, and imaging means having an area camera for imaging a portion illuminated by the slit light are moved relative to one another to image the above workpiece, and the coordinates and brightness of the workpiece are calculated from the pixel data of the area camera to detect the shape and density (or color) of the workpiece and to inspect the shape and appearance of the above workpiece at the same time. Therefore, the shape and appearance of the tire T can be inspected accurately at the same time with a simple structure.

What is claimed is:

1. A method of detecting a workpiece with an apparatus including floodlight means for applying slit light to the surface to be inspected of the workpiece and imaging means having an area camera for imaging a portion illuminated by the slit light relative to one another to image the workpiece, the method comprising the steps of:
   moving a workpiece;
   computing positions of gravity centers of pixels forming image data on the surface of the workpiece imaged by the area camera to obtain coordinates of the workpiece;
   detecting a shape of the workpiece;

computing a brightness of the workpiece by using the brightness of pixels used in computing the positions of the gravity centers; and detecting an appearance of the workpiece from the computed brightness of the workpiece.

2. The method of detecting a workpiece according to claim 1, wherein white slit beams and a color camera are used to detect shape and color of the workpiece at the same time.

3. A method of inspecting a workpiece with an apparatus including floodlight means for applying slit light to the surface to be inspected of the workpiece and imaging means having an area camera for imaging a portion illuminated by the slit light relative to one another to image the workpiece, the method comprising the steps of:

moving a workpiece;

computing positions of gravity centers of pixels forming image data on the surface of the workpiece imaged by the area camera to obtained coordinates of the workpiece;

detecting a shape of the workpiece;

computing a brightness of the workpiece by using the brightness of the pixels used in computing the positions of the gravity centers;

detecting an appearance of the workpiece from the computed brightness of the workpiece; and inspecting the workpiece based on the detected shape and appearance of the workpiece.

4. The method of inspecting a workpiece according to claim 3, wherein coordinates and a brightness of a specific region of the workpiece are integrated to obtain shape data and density data of the specific region.

5. The method of inspecting a workpiece according to claim 4, wherein the obtained shape data or density data is compared with the reference shape data or reference density data on the specific region of the workpiece to inspect the workpiece.

6. The method of inspecting a workpiece according to claim 4, wherein the workpiece is inspected based on surface unevenness calculated from the obtained shape data or the degree of density calculated from the obtained density data.

7. The method of inspecting a workpiece according to claim 4, wherein white slit beams and a color camera are used to detect the shape and a color of the workpiece at the same time.

8. The method of inspecting a workpiece according to claim 3, wherein obtained shape data or density of a specific region data is compared with a reference shape data or reference density data on the specific region of the workpiece to inspect the workpiece.

9. The method of inspecting a workpiece according to claim 8, wherein it is judged that the specific region of the workpiece is unacceptable when the size of a region in which the difference between the obtained shape data and reference shape data and/or the difference between the obtained density data and reference density data exceeds a preset threshold value becomes larger than a predetermined value.

10. The method of inspecting a workpiece according to claim 9, wherein white slit beams and a color camera are used to detect the shape and a color of the workpiece at the same time.

11. The method of inspecting a workpiece according to claim 8, wherein white slit beams and a color camera are used to detect the shape and a color of the workpiece at the same time.

12. The method of inspecting a workpiece according to claim 3, wherein the workpiece is inspected based on surface unevenness calculated from obtained shape data or degree of density calculated from obtained density data.

13. The method of inspecting a workpiece according to claim 12, wherein white slit beams and a color camera are used to detect the shape and a color of the workpiece at the same time.

14. The method of inspecting a workpiece according to claim 3, wherein white slit beams and a color camera are used to detect the shape and a color of the workpiece at the same time.

15. An apparatus for detecting a workpiece, comprising:

floodlight means for applying slit light to the surface to be inspected of the workpiece;

an area camera for imaging a portion illuminated by the slit light;

means of moving the floodlight means, the imaging means and the workpiece relative to one another;

means of computing coordinates of the workpiece from positions of gravity centers of pixels forming image data on the surface of the workpiece imaged by the area camera;

means of detecting a shape of the workpiece from the computed coordinates of the workpiece;

means of computing a brightness of the workpiece by using brightness of pixels used in computing the positions of the gravity centers; and means of detecting an appearance of the workpiece based on the computed brightness.

16. The apparatus for detecting a workpiece according to claim 15, wherein white light is used as the slit light and a color camera is used as the imaging means.

17. An apparatus for inspecting a workpiece, comprising:

the appearance and shape detection apparatus of claim 15;

means of storing reference data on the appearance and shape of the workpiece; and means of judging whether the shape and appearance of the workpiece are acceptable or not by comparing data on the appearance and shape of the workpiece obtained by the appearance and shape detection apparatus with the reference data.

* * * * *